United States Patent
Schneider

(10) Patent No.: US 12,270,876 B2
(45) Date of Patent: Apr. 8, 2025

(54) METHOD AND APPARATUS FOR SUPPRESSING AT LEAST ONE OF AN ELECTRIC OR A MAGNETIC FIELD EMITTED DURING MAGNETIC RESONANCE RECORDINGS

(71) Applicant: Siemens Healthcare GmbH, Erlangen (DE)

(72) Inventor: Rainer Schneider, Hoechstadt (DE)

(73) Assignee: Siemens Healthineers AG, Erlangen (DE)

( * ) Notice: Subject to any disclaimer, the term of this patent is extended or adjusted under 35 U.S.C. 154(b) by 0 days.

(21) Appl. No.: 17/946,302

(22) Filed: Sep. 16, 2022

(65) Prior Publication Data

US 2023/0088438 A1 Mar. 23, 2023

(30) Foreign Application Priority Data

Sep. 21, 2021 (DE) ...................... 10 2021 210 499.1

(51) Int. Cl.
*G01R 33/385* (2006.01)
*A61B 5/055* (2006.01)
(Continued)

(52) U.S. Cl.
CPC ............ *G01R 33/385* (2013.01); *A61B 5/055* (2013.01); *G01R 33/543* (2013.01); *G01R 33/5659* (2013.01)

(58) Field of Classification Search
CPC .............. G01R 33/543; G01R 33/5659; G01R 33/56572; G01R 33/56563;
(Continued)

(56) References Cited

U.S. PATENT DOCUMENTS

2002/0057155 A1 5/2002 Schauwecker et al.
2007/0279060 A1* 12/2007 Dannels ........... G01R 33/56563
324/320
(Continued)

FOREIGN PATENT DOCUMENTS

CN 110610529 A * 12/2019 ............. A61B 5/055
DE 102017213026 A1 1/2019
(Continued)

OTHER PUBLICATIONS

"Active Shimming". Questions and Answers in MRI. Elster LLC. <https://mriquestions.com/active-shimming.html> 2023 (Year: 2023).*
(Continued)

*Primary Examiner* — Rishi R Patel
(74) *Attorney, Agent, or Firm* — Harness, Dickey & Pierce, P.L.C.

(57) ABSTRACT

According to one or more example embodiments, a computer-implemented method for at least partially suppressing a field emitted by a magnetic resonance device during an examination, the emitted field being at least one of an electric field or a magnetic field, the method comprises measuring a signature of the emitted field with a sensor facility; providing a trained function which is configured, based on a signature to generate a field information item relating to the emitted field upon which the respective signature is based; creating a field information item for the emitted field by inputting the signature into the trained function; and suppressing the emitted field by generating a counterfield with a transmitting facility based on the created field information item, the counterfield being at least one of an electric counterfield or a magnetic counterfield, wherein the counterfield is generated such that the counterfield least partially suppresses the emitted field.

22 Claims, 4 Drawing Sheets

(51) Int. Cl.
*G01R 33/54* (2006.01)
*G01R 33/565* (2006.01)

(58) Field of Classification Search
CPC .......................... G01R 33/3875; G01R 33/565; G01R 33/385; G01R 33/5608; G01R 33/422; A61B 5/055
See application file for complete search history.

(56) References Cited

U.S. PATENT DOCUMENTS

| | | | | |
|---|---|---|---|---|
| 2013/0307541 | A1* | 11/2013 | Paul | G01R 33/58 324/318 |
| 2015/0309147 | A1* | 10/2015 | Schmitter | G01R 33/443 600/410 |
| 2018/0253830 | A1* | 9/2018 | Courtney | G06T 5/10 |
| 2019/0033405 | A1 | 1/2019 | Fath et al. | |
| 2020/0249292 | A1* | 8/2020 | Biber | G01R 33/5659 |
| 2021/0007701 | A1 | 1/2021 | Ten Cate et al. | |
| 2021/0192801 | A1 | 6/2021 | Zeller | |
| 2021/0325494 | A1 | 10/2021 | Biber et al. | |
| 2022/0018919 | A1* | 1/2022 | Grodzki | G01R 33/3614 |

FOREIGN PATENT DOCUMENTS

| | | |
|---|---|---|
| DE | 102018205496 A1 | 10/2019 |
| DE | 102019220456 A1 | 6/2021 |
| DE | 102020205037 A1 | 10/2021 |
| EP | 1191345 A2 | 3/2002 |
| EP | 3467531 A1 | 4/2019 |

OTHER PUBLICATIONS

English translation of CN110610529A provided by Espacenet (Year: 2023).*
German Office Action and English translation thereof dated Jul. 9, 2022.
German Decision to Grant and English translation thereof dated Nov. 15, 2022.

* cited by examiner

METHOD AND APPARATUS FOR SUPPRESSING AT LEAST ONE OF AN ELECTRIC OR A MAGNETIC FIELD EMITTED DURING MAGNETIC RESONANCE RECORDINGS

CROSS-REFERENCE TO RELATED APPLICATION(S)

The present application claims priority under 35 U.S.C. § 119 to German Patent Application No. DE 102021210499.1, filed Sep. 21, 2021, the entire contents of which are incorporated herein by reference.

FIELD

One or more embodiments of the present invention relate to a method for active suppression of electric and/or magnetic emissions of a magnetic resonance device and also to a magnetic resonance device with a corresponding suppression apparatus.

BACKGROUND

Magnetic resonance devices (another expression for these is magnetic resonance tomographs) are imaging apparatuses which, for imaging an examination object, align nuclear spins of the examination object with a strong external magnetic field and by an alternating magnetic field, excite them to precession about this alignment. The precession or the return of the spins from this excited state into a state with lower energy itself generates an alternating magnetic field as the response, which is received via antennae.

With the help of magnetic gradient fields, a position encoding is impressed upon the signals, which subsequently enables an allocation of the received signal to a volume element. The received signal is then evaluated and a three-dimensional imaging representation of the examination object is provided. For receiving the signal, preferably local receiving antennae, so-called local coils, are used which, in order to achieve a better signal-to-noise ratio, are arranged directly on the examination object. The receiving antennae can also be installed in a patient support.

SUMMARY

Magnetic resonance devices require radio frequency screening in two regards. Firstly, the magnetic resonance signals to be received for the imaging are extremely weak. In order to achieve a sufficient signal-to-noise ratio (SNR), a screening of external interference signals is required. Conversely, in order to excite the nuclear spins, radio frequency pulses with power levels in the kilowatt range are generated and these are only partially absorbed in the examination object. Radio waves are radiated into the room and must therefore be screened out to maintain emission limit values. Typically, magnetic resonance devices are therefore arranged in a room screened against radio frequency pulses. The provision of such a screened room is not only associated with high costs, but substantially limits the flexibility in the installation of magnetic resonance devices.

One or more embodiments of the present invention provide a method and an apparatus which enable a simpler screening of the electric and/or magnetic field emitted by a magnetic resonance device.

At least one embodiment of the present invention provides a method for at least partially suppressing an electric and/or magnetic field during an examination, a corresponding magnetic resonance device, a method for providing a trained function, a computer program product and a computer-readable storage medium according to the main claim and the subsidiary claims. Advantageous developments are disclosed in the dependent claims.

According to one or more example embodiments, a computer-implemented method for at least partially suppressing a field emitted by a magnetic resonance device during an examination, the emitted field being at least one of an electric field or a magnetic field, the method comprises measuring a signature of the emitted field with a sensor facility; providing a trained function which is configured, based on a signature to generate a field information item relating to the emitted field upon which the respective signature is based; creating a field information item for the emitted field by inputting the signature into the trained function; and suppressing the emitted field by generating a counterfield with a transmitting facility based on the created field information item, the counterfield being at least one of an electric counterfield or a magnetic counterfield, wherein the counterfield is generated such that the counterfield least partially suppresses the emitted field.

According to one or more example embodiments, the created field information item includes at least one of a field profile of the emitted field or one or more field profile parameters which define a field profile of the emitted field; and the generating generates the counterfield such that the counterfield at least partially compensates for the field profile.

According to one or more example embodiments, the created field information item includes at least one of a counterfield profile for at least partially suppressing the emitted field or one or more counterfield profile parameters which define the counterfield profile; and the generating generates the counterfield such that the counterfield corresponds to the counterfield profile.

According to one or more example embodiments, the created field information item comprises one or more control parameters for triggering the transmitting facility to generate the counterfield.

According to one or more example embodiments, the signature comprises an information item relating to the field emitted by the magnetic resonance device in a first spatial region; and the created field information item comprises an information item relating to the field emitted by the magnetic resonance device in a second spatial region, the second spatial region being different from the first spatial region.

According to one or more example embodiments, the created field information item has a greater spatial resolution than a resolution of the emitted field by way of the measured signature.

According to one or more example embodiments, the created field information item provides an information item relating to the emitted field, the information item relating to the emitted field being different from the information item contained in the signature.

According to one or more example embodiments, the suppressing the emitted field takes place in a defined spatial region relative to the magnetic resonance device, and the defined spatial region is different from a recording region of the magnetic resonance device.

According to one or more example embodiments, the measuring measures the signature in a measuring spatial region that is different from the defined spatial region.

According to one or more example embodiments, the measuring spatial region corresponds to a near region; and the defined spatial region corresponds to a far region.

According to one or more example embodiments, the created field information item comprises at least one information item relating to the defined spatial region.

According to one or more example embodiments, computer-implemented method for adjusting a trained function comprised providing a trained function; providing a training signature, wherein the training signature comprises a signature of a field emitted by a magnetic resonance device, the emitted field being at least one of an electric field or a magnetic field; providing a training field information item which characterizes the emitted field which underlies the training signature such that an at least partial suppression of the emitted field occurs by generating a suitable counterfield; generating a field information item by inputting the training signature into the trained function; comparing the generated field information item with the training field information item; and adjusting the trained function based on the comparison.

According to one or more example embodiments, magnetic resonance device comprises a suppression apparatus configured to at least partially suppress a field emitted by a magnetic resonance device during an examination, the field emitted by the magnetic resonance device being at least one of an electric field or a magnetic field, the suppression apparatus including, a computation facility, a sensor facility, and a transmitting facility, each of the sensor facility and the transmitting facility being in signal connection with the computation facility, the sensor facility being configured to measure a signature of the field emitted by the magnetic resonance device, and the transmitting facility being configured to generate a counterfield, wherein the computation facility is configured to, provide a trained function which is configured, based on the signature to generate a field information item relating to the emitted field, generate the field information item by applying the trained function to the signature, and actuate the transmitting facility based on the field information item such that the counterfield generated by the transmitting facility at least partially compensates for the emitted field.

According to one or more example embodiments, a non-transitory computer-readable storage medium has program portions that, when executed by a computation facility, cause the computation facility to perform a method according to one or more example embodiments.

BRIEF DESCRIPTION OF THE DRAWINGS

Features and advantages of the present invention are apparent from the following description of exemplary embodiments, making reference to schematic drawings. Modifications mentioned in this regard can each be combined with one another in order to form new embodiments. In the different figures, the same reference signs are used for the same features.

In the drawings.

DETAILED DESCRIPTION

Figure 1:
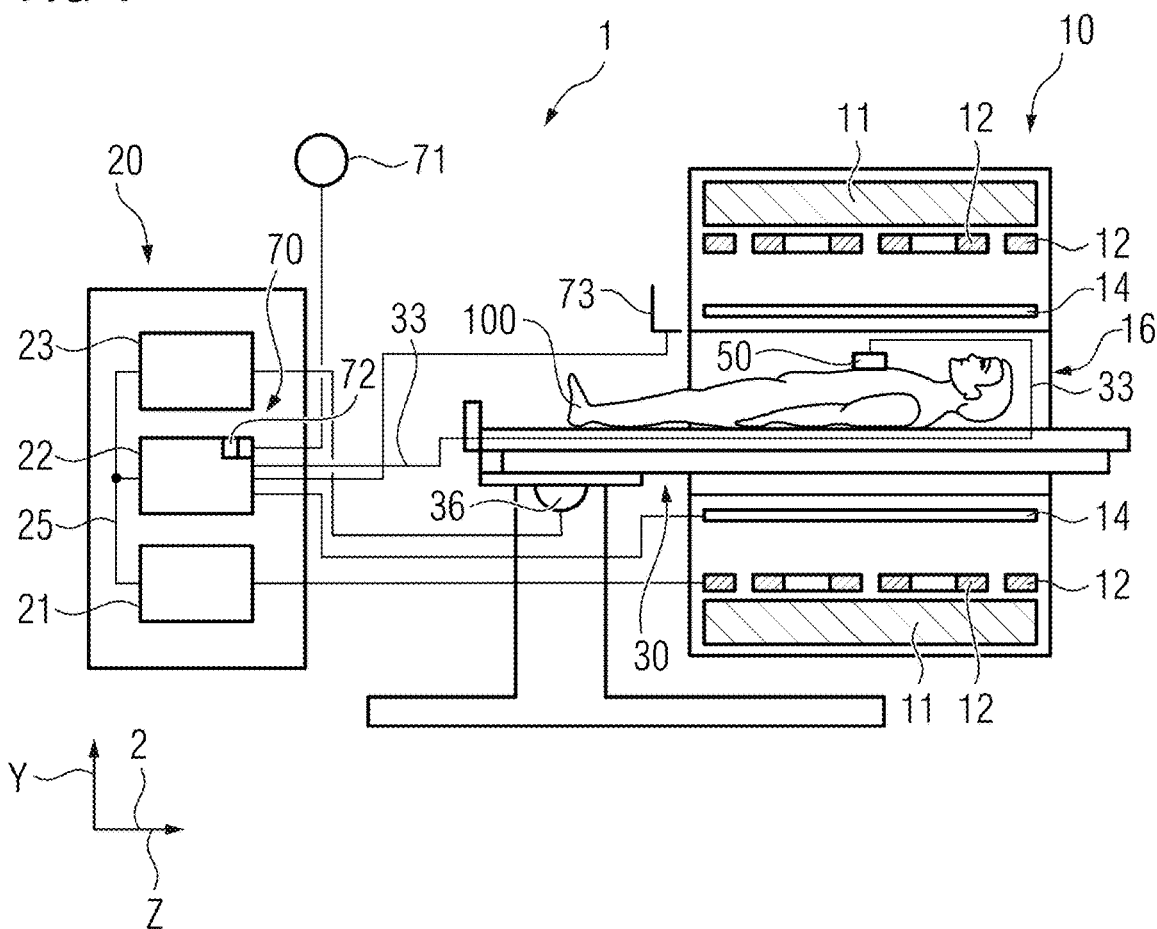
FIG. 1 is a schematic representation in accordance with one embodiment of a magnetic resonance device with a suppression apparatus according to the present invention.

An inventive solution to the problem is described below, both in relation to the claimed method and also in relation to the claimed apparatuses. Features, advantages or alternative embodiments mentioned herein are also transferable similarly to the other claimed subject matter and vice versa. In other words, the present claims (which are directed, for example, to a magnetic resonance device) can also be further developed with the features disclosed or claimed in conjunction with a method. The corresponding functional features of the method are thereby embodied by corresponding physical modules.

Furthermore, the inventive solution to the problem is also described in relation to methods and apparatuses for adjusting trained functions. Herein, features and alternative embodiments/aspects of data structures and/or functions in methods and apparatuses for the determining can be transferred to analogous data structures and/or functions in methods and apparatuses for adjusting. Analogous data structures can herein be characterized, in particular, by the use of the qualifier "training". Furthermore, the trained functions used in methods and apparatuses used for providing the medical information can, in particular, have been adjusted and/or provided, in particular, by methods and apparatuses for adjusting trained functions.

According to one or more example embodiments of the present invention, a computer-implemented method is provided for at least partially suppressing an electric and/or magnetic field emitted by a magnetic resonance device during an examination. The method has a plurality of steps. One step is directed to a measurement of a signature of the emitted electric and/or magnetic field with a sensor facility. A further step is directed to providing a trained function which is configured, on the basis of a signature, to generate a field information item relating to the electric and/or magnetic field upon which the signature is based. A further step is directed to a generation of the field information item by inputting the signature into the trained function. A further step is directed to a suppression of the emitted electric and/or magnetic field by generating an electric and/or magnetic counterfield with a transmitting facility on the basis of the field information item, wherein the counterfield is determined in such a way that it at least partially suppresses the emitted electric and/or magnetic field.

In other words, therefore, a method is provided for active compensation of the electric and/or magnetic field emitted by a magnetic resonance device during an examination. The examination can therein comprise, in particular, a medical imaging method for rendering visible one or more mapping regions in an examination volume of an examination object. For this purpose, the examination object can be introduced into a recording region of the magnetic resonance device. The examination object can be configured, for example, as an anatomical body with one or more hollow spaces. In particular, the examination object can be a patient.

The magnetic resonance device can, in particular, have a field magnet or main field magnet, which generates the static outer magnetic field for aligning the nuclear spins of the examination object or of the patient in a recording region. The magnetic resonance device can further have gradient coils which are designed, for spatial differentiation of the acquired mapping regions in the examination volume of the examination object, to overlay variable magnetic fields onto the static magnetic field in three spatial directions. The magnetic resonance device can also have a body coil (BC) which is designed for radiating a radio frequency signal into the examination volume and for receiving resonance signals emitted from the examination object. Furthermore, the magnetic resonance device can have a suppression apparatus with a transmitting facility which is designed, in particular, for generating a radio frequency electric and/or magnetic counterfield which is intended to compensate outside the recording region, at least partially, for the radio frequency signal emitted by the body coil.

The emitted electric and/or magnetic field can therein denote the electric and/or magnetic field emitted in total by the magnetic resonance device. The expressions electric and/or magnetic field or electric and/or magnetic counterfield can therein denote, in particular, electromagnetic fields and/or alternating electromagnetic fields in the frequency range of the magnetic resonance device. In particular, the emitted electric and/or magnetic field can denote the radio frequency alternating electric and/or magnetic field emitted by the magnetic resonance device. The electric and/or magnetic radio frequency alternating field can therein have contributions generated, in particular, by the body coil and/or the suppression apparatus.

The signature of the emitted electromagnetic field can therein be measured, in particular, by receiving one or more signals of the electric and/or magnetic field emitted by the magnetic resonance device, in particular at a plurality of local sampling points. The receiving of a signal can be understood, in particular, as the recording of an alternating electric and/or magnetic field in the frequency range of the magnetic resonance device and providing it for a subsequent processing. For example, the signature can be received with a sensor facility with one or more receivers or sensors which can be configured, for example, as receiving antennae. The sensor facility is designed, in particular, such that it can record signals of the emitted electric and/or magnetic field at a plurality of different sampling points in the room and/or in the vicinity of the magnetic resonance device. For this purpose, the sensors of the sensor facility can be arranged at different positions in and/or on the magnetic resonance device. The signature can be output by the sensor facility, for example, as a wire-bound electric signal or as a digital, electric, optical or wireless signal. In particular, the signature can have one or more local field variables. The field variables can therein have, in particular, the local field vectors of the emitted electric and/or magnetic field at the sampling points. The field vectors can therein be given by local E-field and H-field vectors.

In other words, the signature measured in this way can thus be understood as a relatively coarse sampling (or a "fingerprint") of the momentarily emitted electromagnetic field which, however, can be generated rapidly and in real time. If a signature of the emitted radio frequency field is generated, both the body coil and also the suppression apparatus or its transmitting facility can make contributions.

The measured signature can therefore only provide an information item at the sampling points. It thereby initially offers no sufficient basis for assessing the emitted electric and/or magnetic field outside the sampling points and subsequently for compensating for and/or suppressing it—for instance, with a counterfield. In order to be able to make a statement regarding the emitted electric and/or magnetic field in the whole spatial region from the locally measured signature (or at least in the spatial region relevant for the screening), it is provided according to one or more example embodiments of the present invention to input the measured signature into a trained function that has been trained on the basis of the signature, to derive a field information item of the electric and/or magnetic field upon which the signature is based. The field information item can, in particular, provide information which enables the electric and/or magnetic field upon which the signature is based to be at least partially suppressed. The field information item can therein be entirely or partially different from the signature. In particular, the field information item can have information in addition to the signature regarding the electric and/or magnetic field. In particular, the field information item can provide information at a greater spatial sampling rate and/or regarding a different spatial region in relation to the magnetic resonance device than the signature. In particular, in some exemplary embodiments, the reference field profile contains field variables, i.e. for example E and H field vectors or generalized field profile parameters (for instance, coefficients of a spherical surface analysis) for spatial points outside the sampling points of the signature. The field information item can be understood as extrapolation or prediction of field properties of the emitted electric and/or magnetic field, starting from the signature. Like the signature, the field information item can relate to the emitted radio frequency field. Similarly to the measured signature, the field information item can further contain contributions of the body coil and/or the suppression apparatus (or its transmitting facility). In particular, the field information item contains field variables for regions in which a compensation or suppression of the electric and/or magnetic field emitted by the magnetic resonance device is to take place—and thus for regions which are not covered spatially by the signature. In particular, the field information item can have a greater spatial resolution or sampling rate of electric and/or magnetic field variables than the measured signature.

In general, a trained function maps input data to output data. Herein, the output data can depend, in particular, upon one or more parameters of the trained function. The one or more parameters of the trained function can be determined and/or adjusted by way of a training process. The determination and/or the adjustment of the one parameter or the plurality of parameters of the trained function can be based, in particular, upon a pair made from training input data and associated training output data, wherein the trained function is applied to the training input data for generating training mapping data. In particular, the determination and/or the adjustment can be based upon a comparison of the training mapping data and the training output data. In general, a trainable function, i.e. a function with as yet non-adjusted parameters, is also designated a trained function.

Other expressions for trained function are trained mapping rule, mapping rule with trained parameters, function with trained parameters, algorithm based upon artificial intelligence, algorithm of machine learning.

An example of a trained function is an artificial neural network. In place of the expression "neural network", the expression "neural net" can also be used. A neural network is in principle constructed like a biological neural network—for instance a human brain. In particular, an artificial neural network comprises an input layer and an output layer. It can also comprise a plurality of layers between the input layer and the output layer. Each layer comprises at least one, preferably a plurality of, nodes. Each node can be understood as a biological processing unit, e.g. as a neuron. In other words, each neuron corresponds to an operation that is applied to input data. Nodes of a layer can be connected by way of edges or connections to nodes of other layers, in particular by way of directed edges or connections. These edges or connections define the data flow between the nodes of the network. The edges or connections are associated with a parameter, commonly designated the "weight" or "edge weight". This parameter can regulate the importance of the output of a first node for the input of a second node, the first node and the second node being connected by way of an edge. In particular, a trained function can also have a deep neural network (or "deep artificial neural network").

In particular, a neural network can be trained. In particular, the training of a neural network is carried out on the basis of the training input data and the associated training output data according to a "supervised" learning technique, wherein the known training input data is input into the neural network and the output data generated by the network is compared with the associated training output data. The artificial neural network learns and adjusts the edge weights for the individual nodes independently for as long as the output data of the last network layer does not sufficiently correspond to the training output data.

According to an exemplary embodiment, the trained function has a convolutional neural network.

A specialist term in the art for a neural network involving convolution is "convolutional neural network". In particular, the convolutional neural network can be configured as a "deep convolutional neural network". The neural network therein has one or more "convolutional layers" and one or more "deconvolutional layers". In particular, the neural network can comprise a collecting layer or "pooling layer". By way of the use of convolutional layers and/or deconvolutional layers, a neural network can be utilized particularly efficiently for image processing since, despite many connections between node layers, only a few edge weights (specifically the edge weights corresponding to the values of the convolution kernel) must be determined. Given an equal number of training data items, the accuracy of the neural network can thereby also be improved.

According to an exemplary embodiment, the trained function has a U-Net architecture.

A U-Net architecture is based upon convolutional neural networks, wherein pooling layers are replaced by "upsampling" layers. Aside therefrom, jump links are provided which enable context information to be input, for example, from convolutional layers directly into deconvolutional layers. By way of the use of a U-Net architecture, a faster processing can be achieved and less training data is needed.

"Providing" the trained function can mean that the trained function can be loaded from a database or is kept ready in a database and/or is hosted in a computation facility. The trained function has therein, in particular, been generated or trained in advance of the examination.

The field information item therefore describes the emission behavior of the magnetic resonance device more completely and in higher resolution than the signature. From the field information item can be derived, in particular, how an electric and/or magnetic counterfield must be constituted in order to compensate for or suppress the adjusted reference field profile or the field variables described therein in a defined spatial region.

The suppression therein takes place by way of a generation of an electric and/or magnetic counterfield which is determined such that it at least partially compensates for the adjusted reference field profile.

If, for example, the radio frequency portions of the electric and/or magnetic emissions of the magnetic resonance device are to be suppressed, a radio frequency counterfield is generated. For this purpose, a transmitting facility is provided. The transmitting facility can have one or more transmitters, for example, in the form of transmitting antennae. If a plurality of transmitting antennae are present, they preferably surround the magnetic resonance device in different spatial directions. It is conceivable, for example, that the counterfield is radiated via one or more transmitting antennae of the transmitting facility as a screening signal. It is conceivable therein to set counterfield parameters such as field strength, phase and/or frequency response dependent upon the field information. The counterfield is therein determined such that the electric and/or magnetic field emitted by the magnetic resonance device is reduced, in particular in a defined spatial region. For example, the phase and amplitude of the counterfield can be set such that the emitted electric and/or magnetic field and the counterfield emitted via the transmitting facility at least partially cancel each other out by destructive interference in the defined spatial region. It is conceivable to optimize the counterfield parameters on the basis of model calculations of the signal propagation on the basis of the geometry of the magnetic resonance device, the arrangement of the transmitting facility, the arrangement of the sensor facility and/or the examination information. In particular, it is therein conceivable that such counterfield parameters have been determined at an earlier time point and are retrieved from a memory store on the basis of the field information item. Alternatively, such counterfield parameters can be provided by the trained function.

By the method described, in particular radio frequency emissions of the magnetic resonance device outside the recording region are actively suppressed and it is possible to operate the magnetic resonance device without providing a screened room. The measurement of the signature with only few local sampling points enables not only a comparatively less complex sensor facility in the vicinity of the magnetic resonance device, but also a rapid capture of the relevant characteristic variables. At the same time, the use of a correspondingly trained function ensures that nevertheless, an assessment of the further-reaching field behavior can be made.

According to one embodiment, the suppression of the emitted electric and/or magnetic field takes place in a defined spatial region relative to the magnetic resonance device.

By this, the suppression of the emitted electric and/or magnetic field does not impair the examination itself. The defined spatial region is different, in particular, from the recording region. Furthermore, the defined spatial region can be different from a near region of the magnetic resonance device. In particular, the defined spatial region can be a far region of the magnetic resonance device, wherein the far region is defined, in particular, as a spatial region beyond a specified distance from the examination volume or from the magnetic resonance device. For example, the specified distance can be 4 to 12 meters and preferably 6 to 10 meters and particularly preferably 8 meters. Therefore, the emitted electric and/or magnetic field is screened in the spatial regions that are at a greater distance from the magnetic resonance device and/or the recording region than the specified distance. The near region can therein adjoin the recording region outwardly from the magnetic resonance device. The far region can therein adjoin the near region outwardly from the magnetic resonance device.

According to one embodiment, the measurement of the signature takes place in a measuring spatial region that is different from the defined spatial region in which the emitted electromagnetic field is to be suppressed.

In particular, the measuring spatial region can be defined as a near region relative to the magnetic resonance device or the recording region. This near region can be defined, for example, as an approximately spherical region with the specified distance as its radius about the recording region or the magnetic resonance device. This has the advantage that the sensor facility for measuring the signature has only to be arranged in the measuring spatial region and, in particular, no complex sensor technology is needed in the far region of the magnetic resonance device. In particular, the measuring spatial region can therein overlap entirely or partially with the defined spatial region (if e.g. a suppression is to take place also in portions of the measuring spatial region).

According to one embodiment, the field information item defines the reference field at least in the defined spatial region and the measuring spatial region.

Thereby, in other words, the field information item creates a bridge between the local sampling points of the emitted electric and/or magnetic field in the near region of the magnetic resonance device and the regions in which subsequently a suppression of the emitted electric and/or magnetic field is to take place.

According to one embodiment, the signature comprises an information item regarding the electric and/or magnetic field emitted by the magnetic resonance device in a first spatial region and the field information item comprises an information item regarding the electric and/or magnetic field emitted by the magnetic resonance device in a second spatial region different from the first spatial region.

Therein, the first spatial region can be a near region of the magnetic resonance device and the second spatial region can be a far region of the magnetic resonance device. In particular, the second spatial region can be the defined spatial region. In particular, the first spatial region can overlap entirely or partially with the second spatial region.

According to one implementation, the step of providing a trained function comprises a selection of a trained function from a plurality of different available trained functions based upon the signature and/or an examination information item relating to the examination.

The available trained functions can be stored, in particular, in a storage facility from which the available trained functions can be retrieved. The storage facility can be designed, for example, as a central storage facility, for instance in the form of a cloud memory store in which trained functions are kept for a wide variety of application cases. By way of the selection, the trained functions that are best suited for the present application case can be loaded from the storage facility. The available trained functions can be specifically adjusted to different possible examination configurations and thus settings and/or configurations of the magnetic resonance device and/or patient properties and/or patient arrangement positions and/or examination rooms and/or types of magnetic resonance devices. According to the implementation it is provided that from the available trained functions, a suitable trained function is selected which is suitable for the generation of the field information item under the given framework conditions. A suitable trained function can be thereby distinguished, for example, in that it has been trained on the basis of data which matches as well as possible the configurations and the respective framework conditions currently being used in the examination. It can therefore be provided in the selection of a suitable trained function to take account of the measured signature and/or an examination information item. The examination information item can comprise, in particular, an information item as to which type of examination is planned for which examination object with which settings of the magnetic resonance device (in particular with which settings of field strengths) based upon which configuration of the magnetic resonance device. The examination information can comprise an information item regarding the examination carried out, the configuration or the type of the magnetic resonance device and/or regarding the patient (age, sex, height, weight, etc.). The examination information item can thus be understood as base information for selecting a trained function. The examination information item can be drawn, for example, directly from the magnetic resonance device and/or received from an information system. The information system can be designed, for example, as a hospital information system (HIS) or a radiology information system (RIS) and can contain, in particular, an examination planning module.

By way of the selection of a trained function from a plurality of available trained functions dependent upon the measured signature and/or an examination information item, the starting situation for the generation of the field information item can be improved. By this, for example, the estimation of the electric and/or magnetic fields in such spatial regions in which an active suppression is to be achieved can be improved. It can be challenging to train a single trained function for all possible circumstances. Furthermore, it is sometimes shown thereby that for certain applications, a trained function with a particular architecture is more suitable than trained functions with other structures. By way of the selection, the suppression of the electric and/or magnetic field can thus ultimately be improved.

The available trained functions can be different in that, for example, they relate to structurally and/or functionally and/or topologically different types or variants of trained functions. Furthermore, the available trained functions can differ in that they have been adjusted on the basis of different training data.

According to one implementation, the field information item comprises a field profile of the emitted electric and/or magnetic field and/or one or more field profile parameters which identify a field profile of the emitted electric and/or magnetic field, wherein the counterfield is determined such that it at least partially compensates for the field profile.

The field profile can comprise, for example, one or more field variables of the emitted electric and/or magnetic field. The field profile can comprise, for example, E and H fields or field vectors of the emitted electric and/or magnetic field. In particular, the field profile can provide field variables at different spatial points around the magnetic resonance device as the signature. Additionally or alternatively, the field information item can comprise field profile parameters which define the underlying electric and/or magnetic field. Such field profile parameters can comprise, for example, one or more location-dependent functions and/or their coefficients which define the emitted electric and/or magnetic field. The field profile parameters can be based, for example, upon a development/approach according to spherical modes or spherical surface functions or upon an estimation of tangential H field vectors on Huygens surfaces (for instance, using "Huygens' Box" methods).

By way of providing a field profile or field profile parameters, an electric and/or magnetic counterfield can be calculated easily with which the emitted electric and/or magnetic field can be at least partially compensated for. Therein the field profile or the field profile parameters also permit a statement to be made regarding spatial regions which are not covered by the signature and consequently an efficient suppression of the emitted electric and/or magnetic field.

According to one implementation, the field information item comprises a counterfield profile which is suitable for at least partially suppressing the emitted electric and/or magnetic field and/or one or more counterfield profile parameters with which a counterfield can be generated (or which define a counterfield profile), which is suitable for at least partially suppressing the emitted electric and/or magnetic field, wherein the counterfield is determined such that it corresponds to the counterfield profile.

In other words, the trained function is directly designed for making a statement regarding a counterfield that can suitably suppress the emitted electric and/or magnetic field. Thereby, a calculation step can be dispensed with and the suppression of the emitted electric and/or magnetic field can be designed to be more efficient. The counterfield profile can therein correspond in its form or configuration to the field profile. Similarly, the counterfield profile parameters can correspond to the field profile parameters in their form or configuration.

According to a further implementation, the field information item comprises one or more control parameters which are suitable to trigger the transmitting facility to generate the electric and/or magnetic counterfield.

Thus, control parameters are output directly by the trained function with which the transmitting apparatus can suitably be actuated. Thus, a rapid and efficient actuation of the transmitting facility and thus a suppression of the emitted electric and/or magnetic field can take place. The control parameters can comprise, for example, control parameters for individual antennae of the transmitting facility. These can be designated cancelation weights. Thus, the components of the transmitting facility can be actuated individually as required.

According to a further aspect, a computer-implemented method for adjusting or providing a trained function is provided. The method comprises a plurality of steps. One step is directed to a provision of a trained function. A further step is directed to providing a training signature, wherein the training signature is a signature of an electric and/or magnetic field emitted by a magnetic resonance device during an examination. A further step is directed to a provision of a training field information item which characterizes the electric and/or magnetic field upon which the training signature is based (wherein the training signature differs from the training field information item). A further step is directed to a generation of a field information item by inputting the training signature into the trained function. A further step is directed to a comparison of the generated field information item with the training field information item. A further step is directed to an adjustment of the trained function on the basis of the comparison.

The training signature therein has the form and configuration of a measured signature as described herein. The training field information item therein has the form and configuration of a field information item as described herein. The training signature and the training field information item can both be derived from the same electric and/or magnetic field of a magnetic resonance device. For example, this field can be sampled for generating a training signature at the measuring points of the later signature. In order to generate the training field information item, the same field values or parameters can be extracted upon which basis a suppression of the field can take place, that is for example, field profiles, field profile parameters, field variables etc. in a spatial region relevant for the suppression. An electric and/or magnetic field upon which a pair constituting the training signature and the training field information item are based can be, for example, an empirically determined, i.e. measured field or a simulated field. Alternatively, starting from such a field, values or parameters of a counterfield can be determined or simulated with which a suitable suppression of the field can be achieved. These values or parameters of a counterfield can be provided, for example, as a counterfield profile, counterfield profile parameters, counterfield field variables as a training field information item. Further alternatively, starting therefrom, control parameters can also be determined or simulated with which a (later to be used) transmitting facility for generating a suitable counterfield can be actuated. Such control parameters can also be provided as a training field information item.

The use of simulated fields as a basis for a training signature and a training field information item has the advantage that training datasets can be generated in effectively any quantity for a wide variety of framework conditions, which can substantially improve the training of the trained function.

In that, on the basis of the training signature, the trained function calculates a field information item which is then compared with the training field information item, the trained function can be successively optimized so that finally it can generate the desired field information item in the required quality. The trained function can therein already be pretrained or can still be entirely untrained.

In a further aspect, a training system for adjusting a trained function is provided. The training system comprises an interface which is designed for receiving the trained function, is further designed for receiving training signatures and associated training field information items, wherein a training signature comprises a signature of an electric and/or magnetic field emitted by a magnetic resonance device and an associated training field information item comprises a field information item of the electric and/or magnetic field which is different from the training signature, which is suitable, in particular, to enable an at least partial suppression of the electric and/or magnetic field. The training system further comprises a computer unit which is designed for determining a field information item based upon the training signature and the trained function (by applying the trained function to the training signature) and is further designed for adjusting the trained function on the basis of a comparison of the field information item with the training field information item.

Such a training system can be designed, in particular, for carrying out the previously described inventive method for adjusting a trained function, and its aspects. The training system is designed for carrying out this method and its aspects in that the interface and the computer unit are designed for carrying out the corresponding method steps.

According to one or more example embodiments of the present invention, a magnetic resonance device with a suppression apparatus is provided, said suppression apparatus being designed for at least partially suppressing an electric and/or magnetic field emitted by the magnetic resonance device during an examination. The suppression apparatus has a computation facility and a sensor facility and a transmitting facility, each being in signal connection with the computation facility. The sensor facility is designed for measuring a signature of the electric and/or magnetic field emitted by the magnetic resonance device, while the transmitting facility is designed for generating an electric and/or magnetic counterfield for at least partial compensation of the emitted electric and/or magnetic field. The computation facility is designed, by applying a trained function to the signature, for generating a field information item, wherein the trained function is designed, on the basis of a signature of an electric and/or magnetic field emitted by a magnetic resonance device, for generating a field information item which relates to the electric and/or magnetic field and, in particular, is different from the signature and furthermore, in particular, is determined such that on the basis of the field information item, a suppression of the emitted electric and/or magnetic field with the transmitting facility can take place. The computation facility is further designed to actuate the transmitting facility on the basis of the field information item such that the counterfield generated by the transmitting facility at least partially compensates for the emitted electric and/or magnetic field.

One or more example embodiments of the present invention relates to the aforementioned suppression apparatus (without a magnetic resonance device).

The sensor facility and the transmitting facility can be designed as described above. The computation facility can, in particular, be designed as part of the control system of the magnetic resonance device. Furthermore, the computation facility can be designed as a decentralized control system separate from the control system of the magnetic resonance device. The computation facility can have one or more control devices and/or one or more processors. In particular, the computation facility can be designed to host the trained function.

The advantages of the proposed magnetic resonance device substantially correspond to the advantages of the proposed method. Features, advantages or alternative embodiments mentioned herein can also be transferred to the other claimed subject matter and vice versa.

According to one embodiment, the suppression apparatus further has a storage facility in signal connection with the computation facility in which storage facility a plurality of trained functions are stored. The computation facility is further designed to provide the trained function by selecting from the stored trained function on the basis of the signature and/or an examination information item relating to the examination.

The storage facility can be designed as a centralized or decentralized database. The storage facility can be, in particular, part of the magnetic resonance device and/or the suppression apparatus. For example, the storage facility can be designed as a computer-readable data carrier of the magnetic resonance device and/or the suppression apparatus. In particular, the storage facility can be designed as an SSD or an HDD hard drive which the computation facility can access. Alternatively, the storage facility can be part of a local server architecture or a cloud storage system.

One or more example embodiments of the present invention relates to a computer program product which comprises a program and can be directly loaded into a memory store of the programmable computation facility and has program means, for example, libraries and auxiliary functions in order to carry out a method for partially suppressing an electric and/or magnetic field emitted by a magnetic resonance device during an examination, in particular according to the aforementioned aspect, when the computer program product is executed.

The computer program product can therein comprise an item of software with a source code which must still be compiled and linked or which must only be interpreted, or an executable software code which, for execution, must only be loaded into the computation facility. By the computer program product, the method can be carried out rapidly, exactly reproducibly and robustly. The computer program product is configured such that it can carry out the method steps according to one or more example embodiments of the present invention by the computation facility. Therein, the computation facility must have the respective pre-conditions such as, for example, a suitable working memory store, a suitable graphics card or a suitable logic unit so that the respective method steps can be carried out efficiently.

The computer program product is stored, for example, on a computer-readable medium or is deposited in a network or server from where it can be loaded into the processor of a computation facility which is directly connected to the computation facility or which can be configured as part of the computation facility. Furthermore, control information of the computer program product can be stored on an electronically readable data carrier. The items of control information of the electronically readable data storage medium can be configured such that they carry out a method according to one or more example embodiments of the present invention when the data storage medium is used in the computation facility. Examples of electronically readable data carriers are a DVD, a magnetic tape or a USB stick, on which electronically readable control information, in particular software, is stored. If these items of control information are read from the data carrier and stored in the computation facility, all the embodiments according to the invention of the above-described methods can be carried out. One or more example embodiments of the present invention can therefore also proceed from the aforementioned computer-readable medium and/or the aforementioned electronically readable data carrier. The advantages of the proposed computer program product substantially correspond to the advantages of the proposed method.

FIG. 1 shows a schematic representation of an embodiment of a magnetic resonance device 1 with a suppression apparatus 70 according to one or more example embodiments of the present invention.

The magnetic resonance device 1 has a magnet unit 10. The magnet unit 10 has a field magnet 11 which generates a static magnetic field B0 for aligning the nuclear spins of samples or of the patient 100 in a recording region AB. The recording region AB is characterized by an extremely homogenous static magnetic field B0, wherein the homogeneity relates, in particular, to the magnetic field strength or the magnitude. The recording region AB is almost spherical and is situated in a patient tunnel 16 which extends in a longitudinal direction 2 through the magnet unit 10. Within the recording region AB, for example, one or more mapping regions can be made visible in an examination volume of the patient. A patient support 30 is movable in the patient tunnel 16 by the displacement unit 36. Typically, the field magnet 11 is a superconducting magnet which can provide magnetic fields with a magnetic flux density of up to 3 T and, in the newest devices, even higher. For weaker field strengths, however, permanent magnets or electromagnets with normally-conducting coils can also be used.

The magnet unit 10 further comprises gradient coils 12 which are designed, for spatial differentiation of the acquired imaging regions in the examination volume, to overlay variable magnetic fields onto the magnetic field B0 in three spatial directions. The gradient coils 12 are typically coils made of normally-conducting wires which can generate mutually orthogonal fields in the examination volume.

The magnet unit 10 also has a body coil 14 which is designed to emit a radio frequency signal fed via a signal line into the examination volume and to receive resonance signals emitted from the patient 100 and to pass them on via a signal line.

A control unit 20 supplies the magnet unit 10 with the different signals for the gradient coils 12 and the body coil 14 and evaluates the received signals.

Thus, the control unit 20 has a gradient controller 21 which is configured to supply the gradient coils 12 via feed lines with variable currents which provide the desired gradient fields in the examination volume in a temporally coordinated manner.

Furthermore, the control unit 20 has a radio frequency unit 22 which is designed to generate a radio frequency pulse with a predetermined temporal sequence, amplitude and spectral power distribution to excite a magnetic resonance of the nuclear spins in the patient 100. Thereby, pulse power levels in the region of kilowatts can be achieved. The excitation pulses can be emitted into the patient 100 via the body coil 14 or via a local transmitting antenna. A control system 23 communicates via a signal bus 25 with the gradient controller 21 and the radio frequency unit 22.

Arranged on the patient 100 as a first receiving coil is a local coil 50 which is connected via a connection line 33 to the radio frequency unit 22 and its receiver. It is also conceivable that the body coil 14 is a part of a sensor facility.

Figure 2:
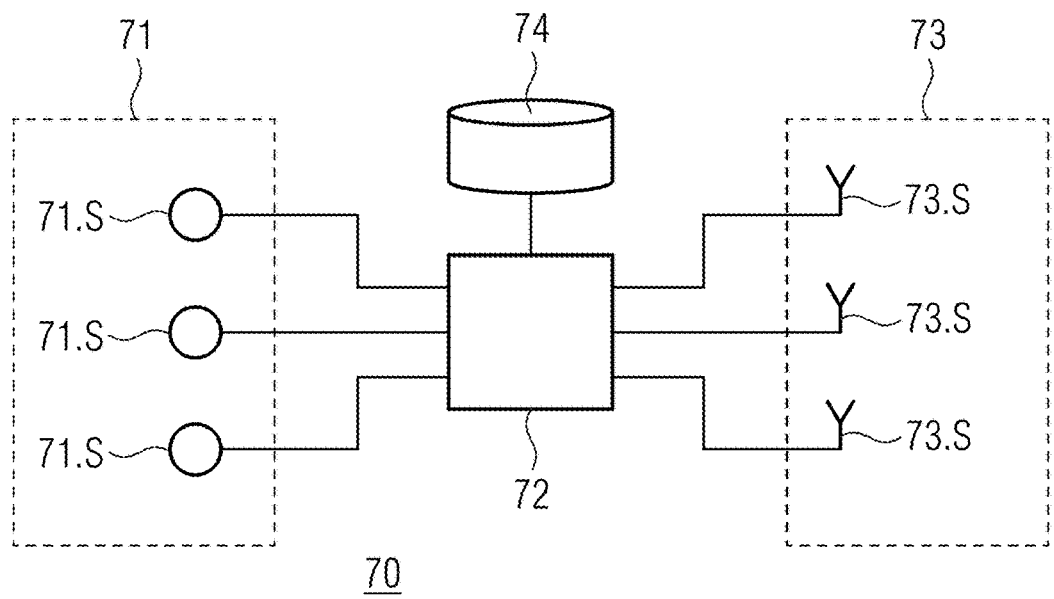
FIG. 2 is a schematic representation of an embodiment of the suppression apparatus in detail.
Figure 3:
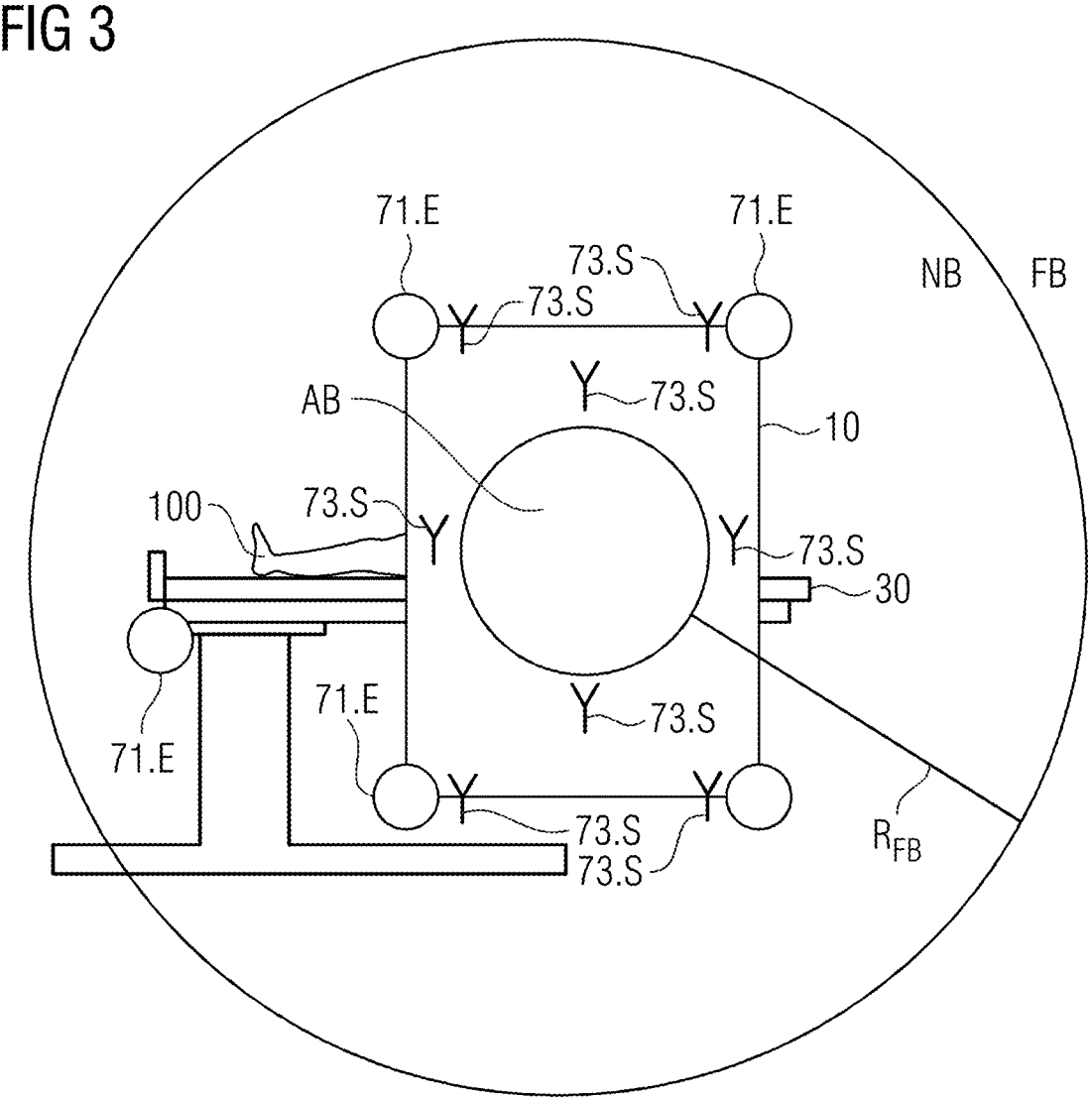
FIG. 3 is a schematic illustration of arrangement positions of transmitting and receiving components of the suppression apparatus on the magnetic resonance device in accordance with one embodiment.

FIG. 2 shows schematically a possible embodiment of the suppression apparatus 70 in detail. The suppression apparatus 70 shown has a sensor facility 71, a computation facility 72, a transmitting facility 73 and a storage facility 74. FIG. 3 shows by way of example, how the components of the suppression apparatus 70 can be arranged relative to the magnetic resonance device 1. Therein, FIG. 3 shows three regions of the magnetic resonance device 1: the recording region AB, a near region NB and a far region FB. The near region NB adjoins the recording region AB outwardly from the magnetic resonance device 1. Furthermore, the recording region AB can also be defined as part of the near region NB. In other words, an arrangement of a component (e.g. the receiver 71.E or the transmitter 73.S) in the near region NB does not preclude it being arranged in the recording region AB. The far region FB adjoins the near region NB externally. The far region FB can therefore be considered to be a spatial region from which the near region NB is excluded. The boundary or boundary surface between the near region NB and the far region FB can be imagined, for example, as a sphere round the magnetic resonance device 1/the recording region AB with a radius RFB, which radius RFB can be several meters in practice. Other forms of the boundary surface are, however, naturally also conceivable, for example, elliptical or cylindrical or combinations thereof. In addition, the near region NB can also overlap with the far region FB.

The computation facility 72 can be designed as part of the device control system of the magnetic resonance device 1, i.e. the control unit 20. Alternatively, the computation facility 72 can be designed as a control device separate therefrom which is assigned exclusively to the suppression apparatus 70. The computation facility 72 can be in data connection with the control unit 20.

The storage facility 74 can have, for example, a computer-readable storage medium that is integrated into the suppression apparatus 70, such as a mass storage facility or a hard disk drive. Alternatively, the storage medium 74 can be designed as a working memory store of the computation facility. Alternatively, the storage facility 74 can have a network memory store with which the computation facility 72 is connected via a network. The network can have, for example, a local area network and/or a wireless local area network. A trained function TF can be provided or hosted in the storage facility 74. The trained function can be designed, in particular, to reconstruct from locally point-wise measured characteristic variables (i.e. the signature S) of an electric and/or magnetic field, field properties as far as the complete field behavior of the respective electric and/or magnetic field. Therein, the trained function TF can be designed to take account of specific cases for the magnetic resonance device 1. The specific cases can relate to specific examinations, configurations and settings of the magnetic resonance device 1. In other words, by way of the use of such a trained function, starting from a measurement carried out spatially through only a few points of an electric and/or magnetic field, field variables of the underlying electric and/or magnetic field can be provided in a different spatial region than only in the measuring points of the signature S and possibly in a higher spatial resolution. Therein, both the emissions of the body coil 14 and also the emissions of the transmitting facility 73 can be taken into account. By way of the trained function TF, therefore, starting from a few measuring points in the framework of the signature S, which has preferably been measured in the near region NB, the electric and/or magnetic field in the entire spatial region and preferably in the far region FB can be predicted.

The information item thus provided by the trained function TF regarding the electric and/or magnetic field is denoted below as a field information item FI. In particular, the field information item FI describes the electric and/or magnetic field both in the near region NB and also in the far region FB (and possibly also in the recording region AB). According to some exemplary embodiments, the field information item FI can contain E and H fields or field vectors of the body coil 14 and the transmitting facility 73 as field variables and so can define the field profile FP of the emitted electric and/or magnetic fields. Additionally or alternatively, the field information item FI can comprise field profile parameters FP-P which sufficiently define the underlying electric and/or magnetic field. Such field profile parameters FP-P can be based, for example on a development/approach according to spherical modes or spherical surface functions or an estimation of tangential H field vectors on Huygens surfaces (for instance, using "Huygens' Box" methods). With a field profile FP or field profile parameters FP-P, an electric and/or magnetic counterfield with which the emitted electric and/or magnetic field can be at least partially compensated for (preferably in the far region FB) can subsequently be calculated.

According to further exemplary embodiments, the field information item FI can equally also comprise a counterfield profile GFP or corresponding counterfield profile parameters GFP-P which relate to an electric and/or magnetic counterfield with which the emitted electric and/or magnetic field can be at least partially compensated for (preferably in the far region FB). The counterfield profile parameters GFP-P can therein have the same form as the aforementioned field profile parameters FP-P.

According to further exemplary embodiments, the field information item FI can also comprise values or control parameters with which the transmitting facility 73 can be actuated so that an electric and/or magnetic counterfield is generated by the transmitting facility 73, which at least partially compensates for the emitted electric and/or magnetic field (preferably in the far region FB). Such values or control parameters can comprise, in particular, so-called cancellation weights. Such values or control parameters can be combined, for example, in a parameter vector which can be input into the transmitting facility 73 and is suitable for actuating the transmitting facility 73 such that a suitable counterfield is generated.

The sensor facility 71 is shown in FIG. 2 by way of example with three receivers 71.E. However, this should not be understood as restrictive. In principle, any desired number of receivers 71.E is conceivable. In particular, just one receiver 71.E can be provided. Preferably, however, the sensor facility 71 has a plurality of receivers 71.E, as shown for example in FIG. 3. The receivers 71.E are therein preferably arranged at different positions in the near region NB of the magnetic resonance device 1. Equally, the transmitting facility 73 preferably has a plurality of transmitters 73.S as shown in FIG. 3. The transmitters 73.S are also preferably arranged in the near region NB. Alternatively, however, the transmitting facility 73 can also have just one transmitter 73.S.

The receivers 71.E of the sensor facility 71 can have antennae which convert an electric and/or magnetic radio frequency alternating field into a current and/or a voltage in a conductor. For example, the antenna can be an induction loop. The electrical signal thus generated is, for example, amplified by a low-noise preamplifier (LNA) in the receiver 71.E itself, before it is passed on via a signal connection into the computation facility 72 for further processing. Alternatively, the sensor facility 71 can have a digital signal processing resource, for example, a digital signal processor DSP or an FPGA. In this exemplary embodiment, the sensor facility 71 already digitizes the signals and passes them on to the computation facility 72. The field variables thus provided to the computation facility 72 are denoted below as $\tilde{E}_{BC}$, $\tilde{H}_{BC}$ for the body coil 14 and as $\tilde{E}_i$, $\tilde{H}_i$ for the transmitter 73.S.

The computation facility 72 is designed to combine the signals of the receivers 71.E of the receiving unit 71, in order thereby to generate a spatially resolved signature S of the radio frequency alternating electric and/or magnetic field emitted by the magnetic resonance device 1. The signature S can therein have matrices of size NA+1×NE for the H and E field, wherein NE denotes the number of the receivers 71.E. The signature S can thus be considered to be a type of fingerprint for the field currently being emitted by the magnetic resonance device 1. The signature S will then depend upon the type of magnetic resonance device 1, the momentary settings of the magnetic resonance device 1, the type of examination currently being carried out (which finds expression in, for example, the position of the patient and the equipment setups used with the magnetic resonance device 1), the room in which the examination takes place and the properties of the patient (height, weight, sex, etc.). These information items are also denoted below as examination information UI.

The computation facility 72 is further designed to apply a trained function TF to the measured signature S. Therein, in some exemplary embodiments, it can optionally be provided that the computation facility 72 initially selects, from a plurality of available (i.e. stored, for example, in the storage facility 74) trained functions TF, that which is best suited for the present case, i.e. has been best trained for the present case. For this purpose, the computation facility can match, for example, the signature S and/or the examination information UI with metadata of the trained function TF that is available and select that from which the best prediction result for the field information item FI is to be expected. For example, in the metadata, the type of magnetic resonance device 1, the manner of the examination, the equipment setups, etc. used, can be recorded for which the respective trained function TF has been adjusted. Alternatively, it is also possible to operate with a single "global" trained function TF which provides good results for all the individual cases.

In any event, through the use of a trained function TF, a field information item is obtained which defines the momentary electric and/or magnetic emissions from the magnetic resonance device 1 not like the signature S at a few selected local measuring points, but spatially highly resolved in different spatial regions AB, NB, FB.

The computation facility 72 is designed, on the basis of this field information item FI, to control the transmitting facility 73 such that the currently emitted electric and/or magnetic field (and here in particular the radio frequency alternating field) is eliminated or at least partially compensated for in defined spatial regions FB. For this purpose, the computation facility 72 can cause the transmitting facility 73 to emit a suitable counterfield G via the transmitter 73.S. Therein, on the basis, for example, of the field information item FI, a suitable phase displacement and weightings of the field components can be determined and mixed to form a counterfield G.

The transmitter 73.S of the transmitting facility 73 can have, for example, antennae, in particular multipart antennae or antenna arrays which can develop, in particular, a directional effect.

In FIG. 3, the arrangement of the transmitter 73.S and the receiver 71.E relative to the magnetic resonance device 1 is shown schematically. With regard to the environment of the magnetic resonance device 1, in principle, as described, a distinction can be made between a near region NB and a far region FB. The magnet unit 10 is—also like the recording region AB—arranged in the near region NB. However, the electromagnetic emissions of the magnetic resonance device 1 also radiate—in any case without countermeasures—into the far region FB. Although the electromagnetic emissions in the far region FB are to be suppressed, a measurement of the electromagnetic emissions in the far region FB is, in practice, often not possible or only with a great effort. However, the use according to one or more example embodiments of the present invention of a trained function TF on local measurements of the electromagnetic fields in the near region NB for predicting the field behavior in the far region FB permits the signature S measured in the near region NB to be "extrapolated" into the far region FB. As shown in FIG. 3, the receivers 71.E can therefore be arranged in the near region NB and, in particular, on the magnetic resonance device 1 or the magnet unit 10 itself. The same applies for the transmitters 73.S. As FIG. 3 shows, the transmitters 73.S and the receivers 71.E are preferably arranged in different directions round the magnetic resonance device 1, in order both in the recording of the signature S and also the emitting of the counterfield G, to ensure the best possible spatial coverage. For example, the receivers 71.E or the transmitters 73.S can be arranged at the "corners" of the magnet unit 10 or on the patient support 30.

Figure 4:
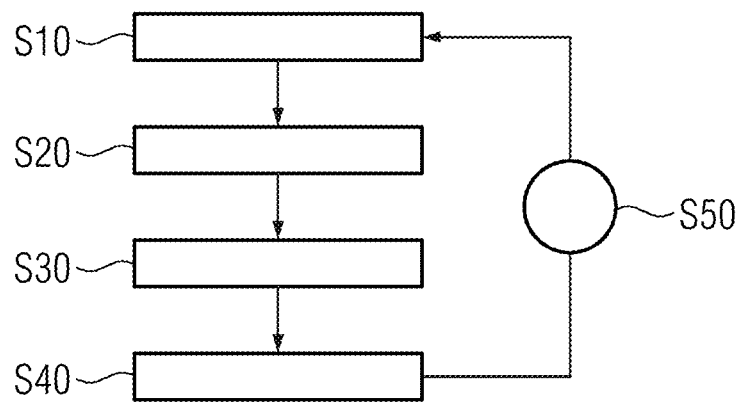
FIG. 4 is a schematic flow diagram for an exemplary embodiment of a method according to the present invention.
Figure 5:
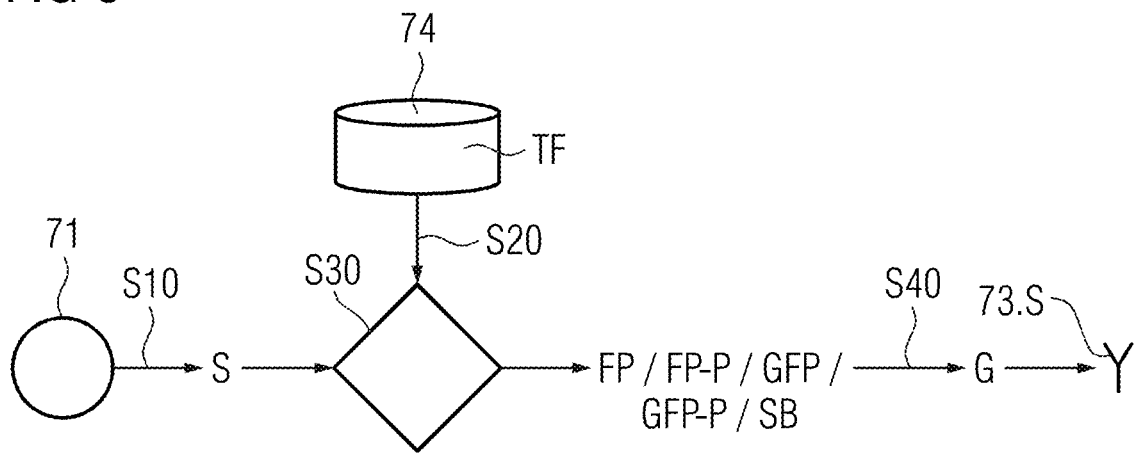
FIG. 5 is a schematic flow diagram which illustrates the progression of the data processing for an exemplary embodiment of the method according to the present invention.

FIG. 4 shows a schematic representation of one embodiment of the proposed method for operating a medical imaging system 1. The sequence of the method steps is not limited either by the sequence shown or by the selected numbering. Thus, the sequence of the steps can be exchanged if relevant and individual steps can be omitted. FIG. 5 shows, for further clarification, a schematic flow diagram which illustrates the progression of the data processing for an exemplary embodiment of the method according to the present invention.

A first step S10 is directed to the measurement of a signature S of the alternating electric and/or magnetic field of the body coil 14 and/or the transmitting facility 73. The measurement takes place in the near region NB by way of the spatially distributed receiver 71.E of the sensor facility 71. Therein, the H and E fields $\tilde{E}_{BC}$, $\tilde{H}_{BC}$ of the body coil 14 and the H and E fields $\tilde{E}_i$, $\tilde{H}_i$ of the transmitter 73.S can be captured (wherein, i=1 to NA). The sites at which these field variables $\tilde{E}_{BC}$, $\tilde{H}_{BC}$, $\tilde{E}_i$, $\tilde{H}_i$ are captured are also denoted hereinafter as dNB.

In a next step S20, a trained function TF is provided. Therein, it can optionally be provided to select from a plurality of available different trained functions TF (in particular, trained for different fields of use). The selection can be made, in particular, on the basis of the signature S measured in step S10 or the aforementioned examination information UI.

In a further step S30, the trained function TF is applied to the measured signature S. In particular, the field variables $\tilde{E}_{BC}$, $\tilde{H}_{BC}$, $\tilde{E}_i$, $\tilde{H}_i$ of the signature S measured at the sites dNB can be input into the trained function TF. The trained function TF is configured such that it maps the measured field variables to a field information item FI which sufficiently identifies the emitted alternating electric and/or magnetic field for the subsequent suppression or which enables a suppression of the emitted alternating electric and/or magnetic field. In particular, a field profile FP can be obtained from which the field variables $\breve{E}_{BC}$, $\breve{H}_{BC}$ of the emitted electric and/or magnetic field can be derived directly in any desired spatial regions. Alternatively, field profile parameters FP-P of the trained function can be output which define the higher-order parameters of the electric and/or magnetic field (such as coefficients of a development according to spherical harmonics) and proceeding from which local field variables $\breve{E}_{BC}$, $\breve{H}_{BC}$ can then be concluded.

In a further step S40, a field information item FI is used to compensate at least partially for the emitted electric and/or magnetic fields, particularly in the far region FB of the magnetic resonance device 1. For this purpose, for example, a counterfield G, in particular, can be determined which is then emitted with the transmitting facility 73. If the field information item FI contains a field profile FP, this can be sampled at any desired locations dFB in the far region and the corresponding field variables $\breve{E}_{BC,1...NA}$, $\breve{H}_{BC,1...NA}$ can be extracted. If the field information item FI contains a field profile parameter FP-P, this parameter can be used accordingly to calculate corresponding field variables $\breve{E}_{BC,1...NA}$, $\breve{H}_{BC,1...NA}$ at least approximately. On this basis, suppression parameters w and v can be calculated, in order to suppress the E and H fields by way of the counterfield G emitted by the transmitting facility 73 in the far region FB below defined limit values $E_{limit}$ and $H_{limit}$ $$\operatorname*{argmin}_{w,v} \begin{pmatrix} \left| \breve{E}_{BC} + \sum_{i=1}^{NA} \breve{E}_i w_i \right| < E_{limit} \\ \left| \breve{H}_{BC} + \sum_{i=1}^{NA} \breve{H}_i v_i \right| < H_{limit} \end{pmatrix}$$

w und v should therein be understood as vectors. The suppression parameters w und v can be, for example, amplification and attenuation factors and the field profile FP can be used thus to provide the counterfield G.

Preferably, a phase shift is also provided. The suppression parameters w and v can also each depend upon the frequency, that is, they can have a spectral dependency. The suppression parameters w and v can therein be determined in different ways. For example, the suppression parameters w and v can be determined analytically or by simulation. The suppression parameters w and v can therein also be stored for known configurations in the computation facility 72 and on determination, retrieved from the memory store. Furthermore, adaptive methods are also conceivable, for example as an optimization problem, wherein by way of the suppression parameters w and v, an energy of the emitted electric and/or magnetic field in the far region FB is minimized. According to some embodiments, the suppression parameters w and v can also be provided directly from the trained function in the form of control parameters.

Alternatively, the trained function TF can also be configured to provide the counterfield profile GFP directly or to provide corresponding counterfield profile parameters GFP-P. On this basis, in step S40 in the computation facility 72, corresponding control commands for the transmitting facility 73 can be determined with which the transmitting facility 73 can be triggered to emit the counterfield G. Alternatively, as stated, such control commands can also be output directly by the trained function TF.

The optional step S50 is embodied, finally, as a repetition step. Following step S40, step S50 leads back to step S10 so that a constant monitoring and suppression of the longer-range emissions of the magnetic resonance device 1 can be reached. Therein, the repetition can be a continuous repetition which runs through the steps S10 to S40 in fixed time cycles. Alternatively, an adaptive repetition of the steps S10 to S40 can be implemented in which a tracking of the suppression apparatus 70 only takes place if substantial changes have taken place in the examination. Such changes can be based, for example, on a changed position of the patient or changed settings on the magnetic resonance device 1. For this purpose, the suppression apparatus 70 can be designed, for example, to monitor the measured signature S continuously and only to undertake a change to the adjusted reference field profile A-RFP if, between individual measuring cycles, deviations lying above a threshold value arise in the measured signature S.

Figure 6:
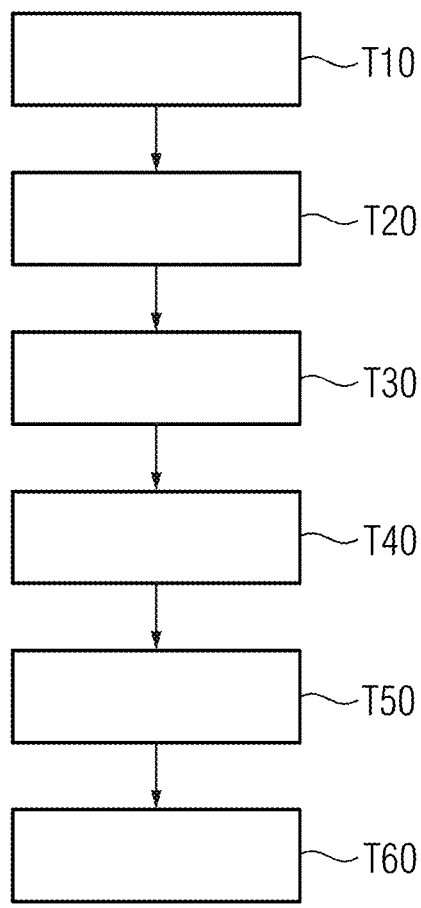
FIG. 6 is a view of a trained function in accordance with an exemplary embodiment.

Shown schematically simplified in FIG. 6 is a trained function TF which is suitable for determining a field information item FI from the measured signature S or can be trained for this. In the exemplary embodiment shown, the trained function TF is configured as a neural network. The neural network can also be designated an artificial neural net, artificial neural network or neural net.

The neural network 100 comprises nodes 120, ..., 129 and edges 140, 141, each edge 140, 141 being a directed connection from a first node 120, ..., 129 to a second node 120, ..., 129. In general, the first node 120, ..., 129 and the second node 120, ..., 129 are different nodes, but it is also possible that the first node 120, ..., 129 and the second node 120, ..., 129 are identical. An edge 140, 141 from a first node 120, ..., 129 to a second node 120, ..., 129 can also be designated an incoming edge for the second node and as an outgoing edge for the first node 120, ..., 129.

The neural network 100 responds to input values x(1)1, x(1)2, x(1)3 to a plurality of input nodes 120, 121, 122 of the input layer 110. The input values x(1)1, x(1)2, x(1)3 are used in order to generate a plurality of outputs x(3)1, x(3)2. The node 120 is connected, for example, via an edge 140 to the node 123. The node 121 is connected, for example, via the edge 141 to the node 123.

In this exemplary embodiment, the neural network 100 learns by adjusting the weighting factors wi, j (weights) of the individual nodes on the basis of training data. Possible input values x(1)1, x(1)2, x(1)3 of the input nodes 120, 121, 122 can be, for example, the individual field variables $\tilde{E}_{BC}$, $\tilde{H}_{BC}$, $\tilde{E}_i$, $\tilde{H}_i$ and/or an examination information item UI (where available).

The neural network 100 weights the input values of the input layer 110 on the basis of the learning process. The output values of the output layer 112 of the neural network 100 preferably correspond to a field information item FI on the basis of which the electric and/or magnetic field upon which the signature S is based can be at least partially suppressed. The output can take place via a single, or a plurality of, output nodes x(3)1, x(3)2 in the output layer 112.

The artificial neural network 100 preferably comprises a hidden layer 111 which comprises a plurality of nodes x(2)1, x(2)2, x(2)3. A plurality of hidden layers can be provided, a hidden layer using output values of another hidden layer as input values. The nodes of a hidden layer 111 perform mathematical operations. An output value of a node x(2)1, x(2)2, x(2)3 therein corresponds to a non-linear function f of its input values x(1)1, x(1)2, x(1)3 and the weighting factors wi, j. After receipt of the input values x(1)1, x(1)2, x(1)3, a node x(2)1, x(2)2, x(2)3 performs a summation of a multiplication, weighted with the weighting factors wi, j, of each input value x(1)1, x(1)2, x(1)3, as determined by the following function:

$$x_j^{(n+1)} = f(\Sigma_i x_i^{(n)} \cdot w_{i,j}^{(m,n)})$$

The weighting factor wi, j can be, in particular, a real number lying, in particular, in the interval [−1;1] or [0;1]. The weighting factor $w_{i,j}^{(m,n)}$ denotes the weight of the edge between the i-th node of an m-th layer 110, 11, 112 and a j-th node of the n-th layer 110, 111, 112.

In particular, an output value of a node x(2)1, x(2)2, x(2)3 is formed as a function f of a node activation, for example, a sigmoid function or a linear ramp function. The output values x(2)1, x(2)2, x(2)3 are transferred to the output node(s) 128, 129. A summation of a weighted multiplication of each output value x(2)1, x(2)2, x(2)3 is calculated anew as a function of the node activation f and thereby the output values x(3)1, x(3)2 are calculated.

The neural network TF shown here is a feedforward neural network in which all the nodes 111 process the output values of a previous layer in the form of its weighted sum as input values. Self-evidently, according to one or more example embodiments of the present invention, other neural network types can be used, for example, feedback networks in which an input value of a node can simultaneously also be its output value.

The neural network TF can be trained by a method of supervised learning in order to provide the field information item. A known procedure is back-propagation which can be applied for all the exemplary embodiments of the present invention. During the training, the neural network TF is applied to training input data or values and must generate corresponding, previously known training output data or values. Mean square errors (MSE) between calculated and expected output values are calculated iteratively and expected output values are calculated and individual weighting factors are adjusted until the deviation between the calculated and expected output values lies below a predetermined threshold.

In order to provide training data, empirical data and/or simulated data can therein be accessed. It is thus conceivable, for example, to arrange the magnetic resonance device 1 in an EMC chamber and to characterize the field emissions with a spatially high-resolution measurement. From this measurement, both the field information item FI and also the associated signature S can be derived. Equally, such information items can be obtained by way of a simulation of the field emissions of the magnetic resonance device 1. Advantageously, the field emissions are measured or simulated separately for all the components of the magnetic resonance device 1 that emit an electric and/or magnetic field and are provided as separate information. Field profiles obtained by way of simulation or measurement depend essentially upon the settings of the magnetic resonance device, upon the examination that is carried out or upon the type and number of additional devices used, the position of the patient and equipment setups of the magnetic resonance device 1. If, for example, parts of a ventilation device enter the recording region AB because the patient needs artificial ventilation, this can have significant effects on the emitted electric and/or magnetic field and therefore on the training field profiles. The same applies for the type, number and arrangement of possible local coils or the configuration and power output of the transmitting facility 73. Further influencing factors relate to the room in which the magnetic resonance device 1 is arranged and in which the examination takes place. Accordingly, the training field profiles should map as many different instances of these configurations as possible. Such information relating to the settings or configurations of the magnetic resonance device 1, the room in which the examination takes place or the manner of the examination or the properties of the patient can be made available as "examination information" UI to the trained function as further input parameters. Alternatively, for different eventuality groups, different trained functions can also be provided which can be more effective in individual situations than a globally trained function TF covering all these conditions, due to their higher level of specialization. In this event, as explained above, a selection step can be provided which selects a suitably trained function for the individual application case.

Figure 7:
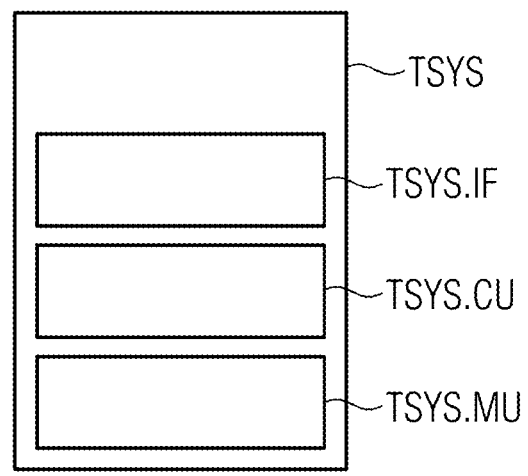
FIG. 7 is a flow diagram of a method for providing a trained function in accordance with an exemplary embodiment.

FIG. 7 shows an exemplary embodiment of a computer-implemented method for providing a trained function TF. The sequence of the method steps is not limited either by the sequence shown or by the selected numbering. Thus, the sequence of the steps can be exchanged, if relevant, and individual steps can be omitted. In addition, one or more steps, in particular, a sequence of steps and optionally the whole method, can be carried out repeatedly.

In step T10, training input data is provided wherein the training input data comprises, in particular, a training signature S and, optionally, an associated examination information item UI. The training signature S therein corresponds to an electric and/or magnetic field emitted by a magnetic resonance device 1 and has preferably been derived from a field profile determined by simulation and/or measurement.

In step T20, training output data is provided, the training output data being related to the training input data and, in particular, comprising a field information item FI that has been prepared in parallel with the determination of the training input data. Therein, the training output data is also based upon the electric and/or magnetic field emitted by the magnetic resonance device 1 and is provided by simulation and/or measurement.

In a step T30, the trained function TF is applied to the training input data in order to generate intermediate output data. The intermediate output data therein corresponds to the field information item FI. The trained function TF can already be pretrained, i.e. one or more parameters of the trained function TF has already been adjusted by the described training method and/or another training method. Alternatively, the one or the plurality of parameters of the trained function can be not yet adjusted by training data, in particular, one or more parameters can be preallocated by way of a constant value and/or a random value. In particular, all the parameters of the trained function TF can be not yet adjusted by training data, in particular, all the parameters can be preset by way of a constant value and/or a random value.

In step 140, this intermediate output data is compared with the training output data, whereupon the trained function TF in step T50 is adjusted on the basis of the comparison. This can take place, for example, on the basis of a cost functional which penalizes deviations of the field information item FI in the intermediate output data from that in the training output data. One or more parameters of the trained function TF can then be adjusted, in particular, so that the cost functional is minimized, for example, by a back propagation. In order to minimize the cost functional, the comparison is carried out for different paired sets from training output data and training output data as well as intermediate output data until a local minimum of the cost functional is achieved and the trained function TF works satisfactorily. In step T60, the thus adjusted trained function TF is finally provided.

Figure 8:
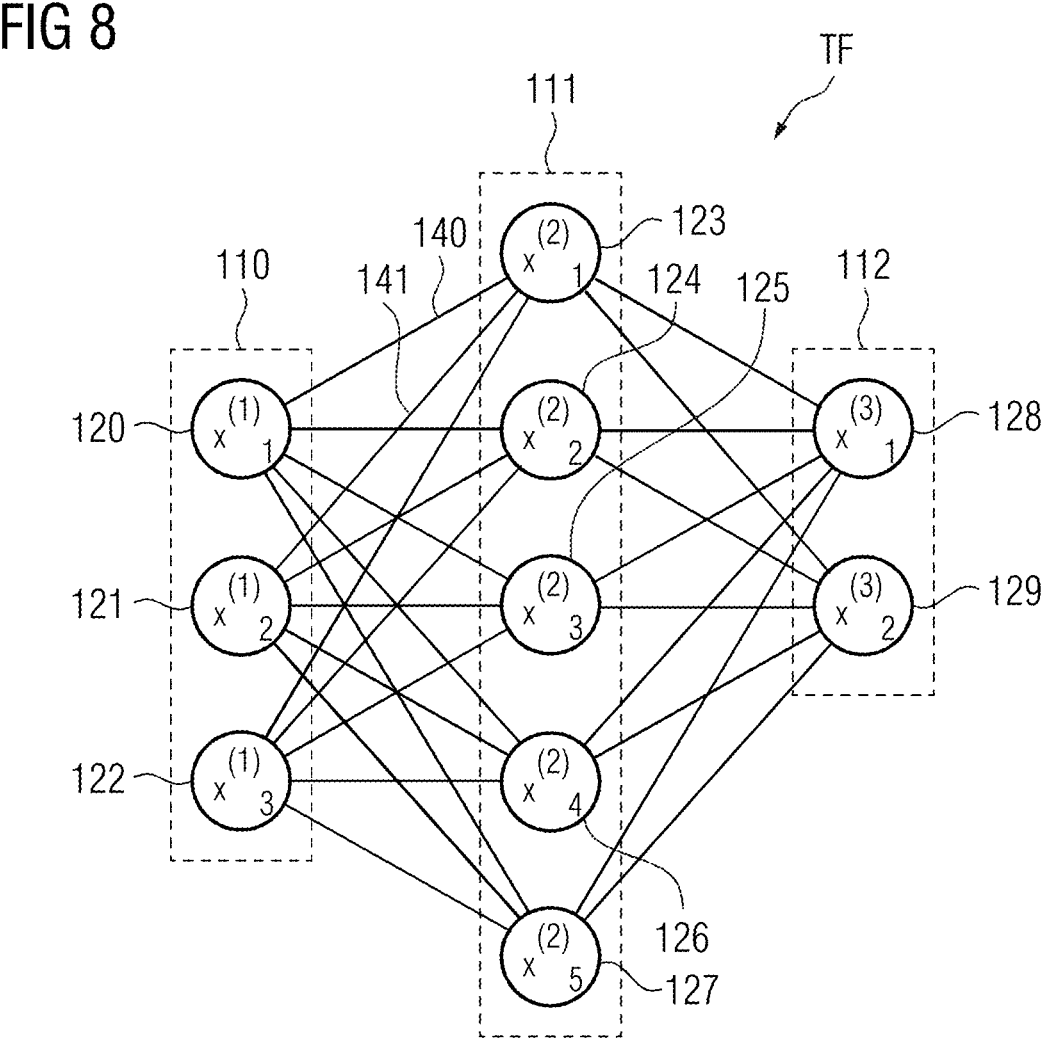
FIG. 8 is a training system for providing a trained function.

FIG. 8 shows a training system ISYS for training a trained function. The training system TSYS shown is configured to carry out one or more example embodiments of the present invention. The training system TSYS comprises an interface TSYS.IF, a computer unit TSYS.CU and a memory unit TSYS.MU. The training system ISYS can be, in particular, a computer, a microcontroller or an integrated circuit. Alternatively, the training system ISYS can be a real or virtual grouping of computers (a technical term therefor being "cluster" or, in the case of a virtual grouping, "cloud"). An interface TSYS.IF can be a hardware or software interface (for example, PCI bus, USB or Firewire). A computer system SYS.CU, TSYS.CU can have hardware elements or software elements, for example, a microprocessor or a so-called FPGA (Field Programmable Gate Array). A storage unit SYS.MU, TSYS.MU can be realized as a non-permanent working memory (Random Access Memory, (RAM)) or as a permanent mass storage unit (hard disk, USB stick, SD card, solid state disk). The training system ISYS shown here is designed to carry out the exemplary embodiments of the method for training a trained function TF in that the interface TSYS.IF and the computer unit TSYS.CU are designed to carry out the respective steps of the method.

Although some example embodiments of the present invention have been disclosed in the form of preferred embodiments and variations thereon, it will be understood that numerous additional modifications and variations could be made thereto without departing from the scope of example embodiments of the present invention. For the sake of clarity, it is to be understood that the use of "a" or "an" throughout this application does not exclude a plurality, and "comprising" does not exclude other steps or elements. The mention of a "unit", "module" or a "device" does not preclude the use of more than one unit or device.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'unit', interface' or the term 'controller' may be replaced with the term 'circuit.' The term 'module' and may 'unit' refer to, be part of, or include processor hardware (shared, dedicated, or group) that executes code and memory hardware (shared, dedicated, or group) that stores code executed by the processor hardware.

The module or interface may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices (i.e., storage means). The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non- volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where it has not yet explicitly been set out, although useful and in the context of the present invention, individual sub-aspects or features thereof can be combined and/or exchanged with one another without departing from the scope of the present invention. Advantages of the present invention described in relation to an exemplary embodiment also apply, where transferrable, to other exemplary embodiments without this being explicitly stated.

The invention claimed is:

1. A computer-implemented method for at least partially suppressing an emitted field, the emitted field being emitted by a magnetic resonance device during an examination, the emitted field being at least one of an electric field or a magnetic field, and the method comprising:
    measuring a signature of the emitted field with a sensor facility;
    providing a trained function configured to generate a field information item based on the signature, the field information item relating to the emitted field on which the signature is based;
    creating the field information item for the emitted field by inputting the signature into the trained function to obtain a created field information item; and
    suppressing the emitted field by generating a counterfield based on the created field information item, the counterfield being generated with a transmitting facility, the counterfield being at least one of an electric counterfield or a magnetic counterfield, the counterfield being generated such that the counterfield at least partially suppresses the emitted field, the suppressing the emitted field taking place in a defined spatial region relative to the magnetic resonance device, and the defined spatial region being different from a recording region of the magnetic resonance device.

2. The method of claim 1, wherein
    the created field information item includes at least one of a field profile of the emitted field or one or more field profile parameters, the one or more field profile parameters defining the field profile of the emitted field; and
    the generating generates the counterfield such that the counterfield at least partially compensates for the field profile.

3. The method of claim 2, wherein
    the signature comprises an information item relating to the emitted field in a first spatial region; and
    the created field information item comprises an information item relating to the emitted field in a second spatial region, the second spatial region being different from the first spatial region.

4. The method of claim 2, wherein
the created field information item has a greater spatial resolution of the emitted field than a spatial resolution of the signature.

5. The method of claim 2, wherein
the created field information item provides a first information item relating to the emitted field, the first information item being different from a second information item contained in the signature.

6. The method of claim 1, wherein
the created field information item includes at least one of:
a counterfield profile for at least partially suppressing the emitted field, or
one or more counterfield profile parameters which define the counterfield profile; and
the generating generates the counterfield such that the counterfield corresponds to the counterfield profile.

7. The method of claim 1, wherein
the created field information item comprises one or more control parameters for triggering the transmitting facility to generate the counterfield.

8. The method of claim 1, wherein
the signature comprises an information item relating to the emitted field in a first spatial region; and
the created field information item comprises an information item relating to the emitted field in a second spatial region, the second spatial region being different from the first spatial region.

9. The method of claim 1, wherein
the created field information item has a greater spatial resolution of the emitted field than a spatial resolution of the signature.

10. The method of claim 1, wherein
the created field information item provides a first information item relating to the emitted field, the first information item being different from a second information item contained in the signature.

11. The method of claim 1, wherein
the measuring measures the signature in a measuring spatial region that is different from the defined spatial region.

12. The method of claim 11, wherein
the measuring spatial region corresponds to a near region; and
the defined spatial region corresponds to a far region.

13. The method of claim 11, wherein
the created field information item comprises at least one information item relating to the defined spatial region.

14. A non-transitory computer-readable storage medium having program portions that, when executed by a computation facility, cause the computation facility to perform the method of claim 1.

15. The method of claim 1, wherein the defined spatial region is outside of the recording region.

16. The method of claim 15, wherein the recording region is in a patient tunnel of the magnetic resonance device.

17. The method of claim 1, wherein the defined spatial region is outside of the magnetic resonance device.

18. The method of claim 1, wherein the generating the counterfield is performed by the transmitting facility using at least one antenna through which the counterfield is emitted.

19. The method of claim 18, wherein the at least one antenna is outside of the magnetic resonance device.

20. The method of claim 1, wherein the signature includes a first field vector of the emitted field.

21. The method of claim 1, wherein the created field information item includes at least one of:
a second field vector of the emitted field;
parameters of the second field vector;
a third field vector of the counterfield;
parameters of the third field vector; or
one or more control parameters for triggering the transmitting facility to generate the counterfield, the one or more control parameters including cancellation weights.

22. A magnetic resonance device comprising:
a suppression apparatus configured to at least partially suppress an emitted field, the emitted field being emitted by a magnetic resonance device during an examination, the emitted field being at least one of an electric field or a magnetic field, and the suppression apparatus including,
a computation facility,
a sensor facility, and
a transmitting facility, each of the sensor facility and the transmitting facility being in signal connection with the computation facility, the sensor facility being configured to measure a signature of the emitted field, and the transmitting facility being configured to generate a counterfield, wherein the computation facility is configured to,
provide a trained function configured to generate a field information item based on the signature, the field information item relating to the emitted field,
generate the field information item by applying the trained function to the signature to obtain a created field information item, and
actuate the transmitting facility based on the created field information item such that the counterfield generated by the transmitting facility at least partially suppresses the emitted field in a defined spatial region relative to the magnetic resonance device, the defined spatial region being different from a recording region of the magnetic resonance device.

* * * * *